(12) United States Patent
Peruvingal

(10) Patent No.: US 7,648,473 B1
(45) Date of Patent: Jan. 19, 2010

(54) TRACTION EXTENSION TABLE

(76) Inventor: Jedheesh Peruvingal, 6 Gerard Ave., New Hyde Park, NY (US) 11040

( * ) Notice: Subject to any disclaimer, the term of this patent is extended or adjusted under 35 U.S.C. 154(b) by 356 days.

(21) Appl. No.: 11/522,715

(22) Filed: Sep. 18, 2006

(51) Int. Cl.
*A61F 5/00* (2006.01)
*A47B 7/00* (2006.01)
*A61H 1/00* (2006.01)
*A61H 1/02* (2006.01)

(52) U.S. Cl. .............................. 602/32; 602/39; 5/613; 5/617; 601/24; 606/241

(58) Field of Classification Search .................. 602/32, 602/39; 606/241, 245; 5/613–618; 601/23–26, 601/90, 98
See application file for complete search history.

(56) References Cited

U.S. PATENT DOCUMENTS

| 326,247 | A | | 9/1885 | Root |
|---|---|---|---|---|
| 1,966,448 | A | | 7/1934 | Kabisius |
| 2,494,094 | A | | 1/1950 | Horstman |
| 2,598,204 | A | | 5/1952 | Allen |
| 3,644,946 | A | | 2/1972 | Swatt |
| 4,258,445 | A | * | 3/1981 | Zur .............................. 5/614 |
| 5,106,079 | A | | 4/1992 | Escobedo et al. |
| 5,178,593 | A | | 1/1993 | Roberts |
| 5,269,736 | A | | 12/1993 | Roberts |
| 6,090,022 | A | | 7/2000 | Colecchi |
| 6,506,174 | B1 | * | 1/2003 | Saunders et al. .............. 602/33 |
| 6,764,432 | B2 | | 7/2004 | Hippensteel |
| 6,839,926 | B2 | * | 1/2005 | Heimbrock et al. ............ 5/618 |
| 6,971,997 | B1 | * | 12/2005 | Ryan et al. ..................... 602/32 |

FOREIGN PATENT DOCUMENTS

| CA | 2280303 | 8/1999 |
|---|---|---|
| GB | 2118849 | 11/1983 |

* cited by examiner

*Primary Examiner*—Patricia M Bianco
*Assistant Examiner*—Keri J Nicholson
(74) *Attorney, Agent, or Firm*—Michael I Kroll

(57) ABSTRACT

A traction extension table used to aid the user in performing assisted lower back and abdominal extensions for the treatment of bulging/herniated lumbar discs. The table has a frame constructed utilizing a plurality of cushioned sections forming the table's top with one movable along a roller assembly mating with the table frame for section relocation and releasable securement upon relocation. Another is contoured to have table frame supported hand-placement supports at the head. The contoured cushion is hingedly attached to the table frame and also connected to at least one shock absorber. To better accommodate the user, the pads have lumbar and chest harnesses to keep the user in position while performing an exercise while the chest pad has a face hole to accommodate the user's nose while lying face down on the table.

Figure 1:
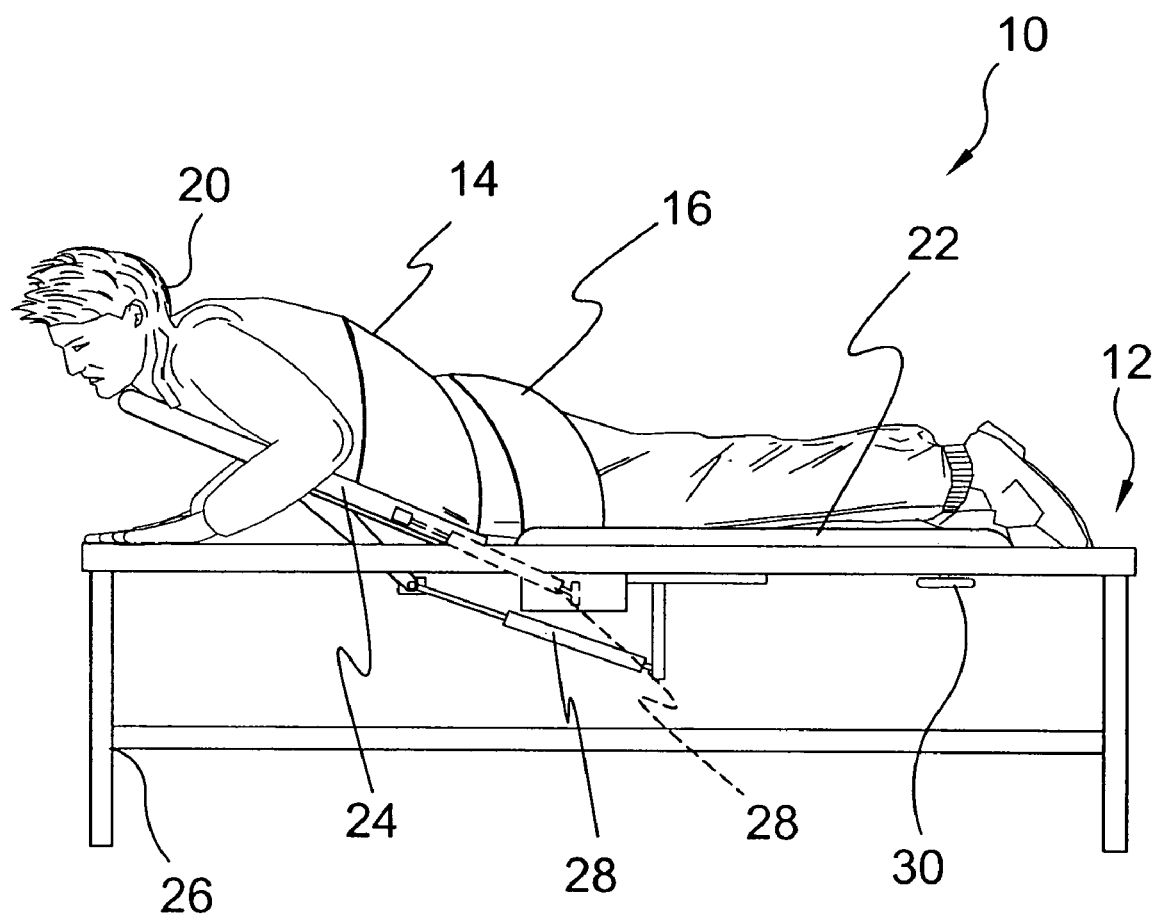

14 Claims, 11 Drawing Sheets

TRACTION EXTENSION TABLE

BACKGROUND OF THE INVENTION

1. Field of the Invention

The present invention relates generally to exercise equipment and, more specifically, a traction extension table used to aid the user in performing assisted lower back and abdominal extensions for the treatment of bulging/herniated lumbar discs.

The table having a frame is constructed utilizing a plurality of cushioned sections forming the table's top with one movable along a roller assembly mating with the table frame for section relocation and releasable securement upon relocation. Another is contoured to have table frame supported hand-placement supports at the head. The contoured cushion is hingedly attached to the table frame and also connected to at least one shock absorber.

To better accommodate the user, the pads have lumbar and chest harnesses to keep the user in position while performing an exercise while the chest pad has a face hole to accommodate the user's nose while lying face down on the table.

In operation a user exercises by placing their hands on the hand supports and pushing up arching their back while the shock absorber extends and controls the rate of descent as the user returns to the starting exercise position.

The upper chest harness is attached under the table via springs to maintain the traction as the hinged table section pivots up.

2. Description of the Prior Art

There are other exercising devices designed for aiding physical development. Typical of these is U.S. Pat. No. 326,247 issued to J. B. Root on Sep. 15, 1885.

Another patent was issued to C. W. Kabisius on Jul. 17, 1934 as U.S. Pat. No. 1,966,448. Yet another U.S. Pat. No. 2,494,094 was issued to W. G. Horstman on Jan. 10, 1950 and still yet another was issued on May 27, 1952 to R. E. Allen as U.S. Pat. No. 2,598,204.

Another patent was issued to Leonard W. Swatt on Feb. 29, 1972 as U.S. Pat. No. 3,644,946. Yet another U.S. Pat. No. 5,106,079 was issued to Harold J. Escobedo on Apr. 21, 1992. Another was issued to Mark J. Roberts on Jan. 12, 1993 as U.S. Pat. No. 5,178,593 and still yet another was issued on Dec. 14, 1993 to Mark J. Roberts as U.S. Pat. No. 5,269,736.

Another patent was issued to Anthony P. Colecchi on Jul. 18, 2000 as U.S. Pat. No. 6,090,022. Yet another U.S. Pat. No. 6,764,432 was issued to Joseph B. Hippensteel on Jul. 20, 2004. Another was issued to Alan Herrod on Apr. 24, 1982 as British Patent No. GB2118849 and still yet another was issued on Feb. 18, 2001 to Michael Allen Ralph as Canadian Patent No. CA2280303.

U.S. Pat. No. 326,247

Inventor: J. B. Root

Issued: Sep. 15, 1885

In an exercising-machine, the combination of a flywheel and a handle or handles connected by a crank with and for operating said flywheel, as and for the purposes set forth.

U.S. Pat. No. 1,966,448

Inventor: C. W. Kabisius

Issued: Jul. 17, 1934

In a mechanical swimming instructor, the combination of a frame, a cam mounted on one side of the frame and another cam mounted on the other side of the frame, each of said cams having a continuous path with an upper portion disposed in one plane and a lower portion disposed in one plane and a lower portion disposed in a plane extending at an angle to the plane of the upper portion, an offset arm-bracket supported in the angle between the said planes and having a pivotal joint, means for connecting the pivotal joint, means for connecting the pivotal joints so that the arm-bracket on one side of the frame moves in synchronism with the arm-bracket on the other side, an arm carried by each bracket for supporting the arm of the swimmer and means for guiding each bracket for supporting the arm of the swimmer and means for guiding each arm bracket on its corresponding cam, said arm brackets being disposed so that when guiding means of one arm is running on the upper portion of one cam and guiding means of the other arm is running on the lower portion of the other cam.

U.S. Pat. No. 2,494,094

Inventor: W. G. Horstman

Issued: Jan. 10, 1950

An exercising device comprising a base member, a body supporting member, an upright coil spring connected between said two members having and end coil arranged in a plane substantially normal to the axis of said spring, means for connecting said end coil with one of said two members including a clamp member having an annular curved portion adapted to receive one side of said end coil therein, with said one member having an annularly depressed portion adapted to receive the other side of said end coil, with said clamp member being positionable opposite said depressed portion to substantially close said end coil therebetween, and means for clamping said end coil between said depressed portion and said clamp member.

U.S. Pat. No. 2,598,204

Inventor: R. E. Allen

Issued: May 27, 1952

In an exercising apparatus, a fixed section having a substantially horizontal supporting surface, a leaf hinged to said fixed section at one side of said supporting surface, being placeable in the same plane therewith and at various inclinations above and below that plane, a lever pivoted to the fixed section below the connection between the leaf and fixed section, extending thence under the leaf and bearing thereon at a considerable distance from the pivot of the leaf, a motor cylinder, and an extensible member movable into and out of said cylinder coupled to said lever at an intermediate point between the pivot thereof and the part which bears on the leaf, said lever causing an augmented movement to be transmitted to the leaf from the motor.

U.S. Pat. No. 3,644,946

Inventor: Leonard W. Swatt

Issued: Feb. 29, 1972

An adjustable bed comprising a rectangular frame on which are mounted rigid bedboard sections supporting a coil spring directly thereon. The bedboard comprises a stationary seat section mounted on the frame, and head and thigh sections pivoted at fixed points relative to the frame and seat section and tiltable relative thereto. A foot section is pivoted levers and the head and thigh sections have lever arms pivotally mounted thereon at one end and carrying rollers at their opposite ends mounted on trackways on the frame. Separate motor actuators individually rotate the arms pivotally mounted on the head and thigh bedboard sections to tilt them as the head and thigh bedboard sections to tilt them as the rollers ride on the trackways on the frame. The actuators are individually operated in opposite directions to adjust the bed by manual control.

U.S. Pat. No. 5,106,079

Inventor: Harold J. Escobedo

Issued: Apr. 21, 1992

Exercise apparatus enables a person to perform extended push-ups with a variable and adjustable weight on his back. The apparatus includes a frame with elevated longitudinal members carrying handles near their forward ends. A weight platform is pivotally supported near the rear end of the frame. A locking arrangement manipulated by the feet of the user selectively locks or unlocks the weight platform against downward movement.

U.S. Pat. No. 5,178,593

Inventor: Mark J. Roberts

Issued: Jan. 12, 1993

Disclosed is an exercise apparatus that is a combination stationary recumbent cycle-type exerciser and an upper body exerciser, and a method of exercising. In the stationary recumbent cycle mode, the seated operator pedals a conventional pedal mechanism. In the upper body exerciser mode, the operator is in a normal push-up position with the hands on the pedals of the pedal mechanism. Exercising is accomplished by hand pedaling the pedal mechanism while supporting the body weight on the feet and hands. The machine has an adjustment to help support the operator's chest with a chest pad.

U.S. Pat. No. 5,269,736

Inventor: Mark J. Roberts

Issued: Dec. 14, 1993

Disclosed is an exercise apparatus that is a combination stationary recumbent cycle-type exerciser and an upper body exerciser, and a method of exercising. In the stationary recumbent cycle mode, the seated operator pedals a conventional pedal mechanism. In the upper body exerciser mode, the operator is in a normal push-up position with the hands on the pedals of the pedal mechanism. Exercising is accomplished by hand pedaling the pedal mechanism while supporting the body weight on the feet and hands. The machine has an adjustment to help support the operator's chest with a chest pad.

U.S. Pat. No. 6,090,022

Inventor: Anthony P. Colecchi

Issued: Jul. 18, 2000

An exercise apparatus for exercising a user's stomach, back and leg muscles. The exercise apparatus includes a base frame with a front post upwardly extending therefrom. A bench is pivotally coupled to the base frame and attached to the front post. A backrest is pivotally coupled to the bench. A motor with a pair of opposite outwardly extending rotating shafts is mounted under the bench. A pair of side posts upwardly extend from the base frame and each have a pulley rotatably mounted thereto. Each of the rotating shafts has a spool coupled thereto. A pair of elongate flexible cables are coupled to the backrest with a first of the cables looped around one of the pulleys and wound around one of the spools and a second of the cables looped around the other of the pulleys and wound around the other of the spools.

U.S. Pat. No. 6,764,432

Inventor: Joseph B. Hippensteel

Issued: Jul. 20, 2004

An antigravity full range of motion four limb dry swim overall body exercise machine that allows virtually every muscle in the body to work anaerobically or aerobically, at the user's choosing, while the user is lying down on their back to take pressure off the user's spine, and working most muscles through a nominal or up to a full range of motion at the user's choosing, which motions can be in one of several directions or arcs at the user's choosing. The machine includes a base frame with parallel frame adjustable lengths and supporting cross segments horizontally and vertically to a second parallel frame length above the first, the entire base frame having a first end and a second end, the first end having frame adjustments to accept length and tension adjustable arm apparatuses with handles, the second end having frame adjustments to accept length and tension adjustable leg apparatuses with pedals. Mounted on top of the base frame top parallel lengths are padded bench apparatuses, one for the torso which can include a headrest and one for the hips. The middle of the length of the base frame has a spring or shock absorber type structure to allow the middle top level of the base frame, supporting the seat and torso apparatuses, to have an up and down motion to allow for abdominal flexion of the user permitted by a pivoting action of the seat and torso apparatus sections of the upper level of the base frame. The seat and torso apparatus sections are permitted to pivot in a seesaw type action by a fulcrum cross piece under and supporting the center of each bench section.

U.K Patent Number GB2118849

Inventor: Alan Herrod

Issued: Apr. 24, 1982

The bench, for use when practicing swimming strokes out of water, comprises a main body support 7 on a stand 1, and a back/chest support 13 extending from one end of the main support and pivotable about a longitudinal axis of the main support. The back/chest support 13 is freely rotatable and provided with alternative surface profiles on opposite faces to suit practice in different strokes such as back stroke and crawl. The bench can be used with a pulley exercise machine.

Canadian Patent Number CA2280303

Inventor: Michael Allen Ralph

Issued: Aug. 18, 1999

An exercise apparatus, more particularly an exercise bench for supporting a user doing a push-up. The bench allows the user to keep its body straight while performing push-ups, thereby isolating the arms, chest and back. The bench is adjustable to distribute some of the weight of the user onto a support and thus increase or decrease the weight a user is lifting during the incline of the push-up. It also has an adjustable biasing member for adjusting the weight on the decline of the push-up. The apparatus is collapsible for easy storage.

While these exercise devices may be suitable for the purposes for which they were designed, they would not be as suitable for the purposes of the present invention, as hereinafter described.

SUMMARY OF THE PRESENT INVENTION

A primary object of the present invention is to provide an exercise table used for the treatment of bulging/herniated lumbar/thoractic discs having a plurality of pads one being angular and longitudinally adjustable and the other being set on rollers for lateral accommodation of ones body while performing an exercise.

Another object of the present invention is to provide an exercise table used for assistance in performing extension exercise for the treatment of bulging/herniated having a chest harness attached under the top portion of the table via springs to maintain traction to the lumbar spine while the table comes up.

Yet another object of the present invention is to provide an exercise table used for the treatment of bulging/herniated lumbar discs having rollers bound to a track with a locking mechanism for stabilization of said rollers in the track to give traction to the lumbar spine.

Still yet another object of the present invention is to provide an exercise table used for assistance with extension exercise having a pad outfitted with a face hole to accommodate ones face while performing an exercise lying face down.

Another object of the present invention is to provide an exercise table used for assistance with extension exercise for the treatment of bulging/herniated discs having two harnesses that will maintain traction to the lumbar spine while the user performs the extension exercise.

Additional objects of the present invention will appear as the description proceeds.

The present invention overcomes the shortcomings of the prior art by providing a segmented table having means for providing a user an exercise table used for assistance in lower back and abdominal development having harnesses for situating the user nose holes to accommodate ones face. Additionally the table has a portion of padding that is laterally adjustable on rollers that may be locked utilizing a locking mechanism to provide traction to the lumbar spine from waist below, traction from above waist is maintained by chest harness attached to the under part of the table via spring to give traction for lumbar spine.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

Figure 2:
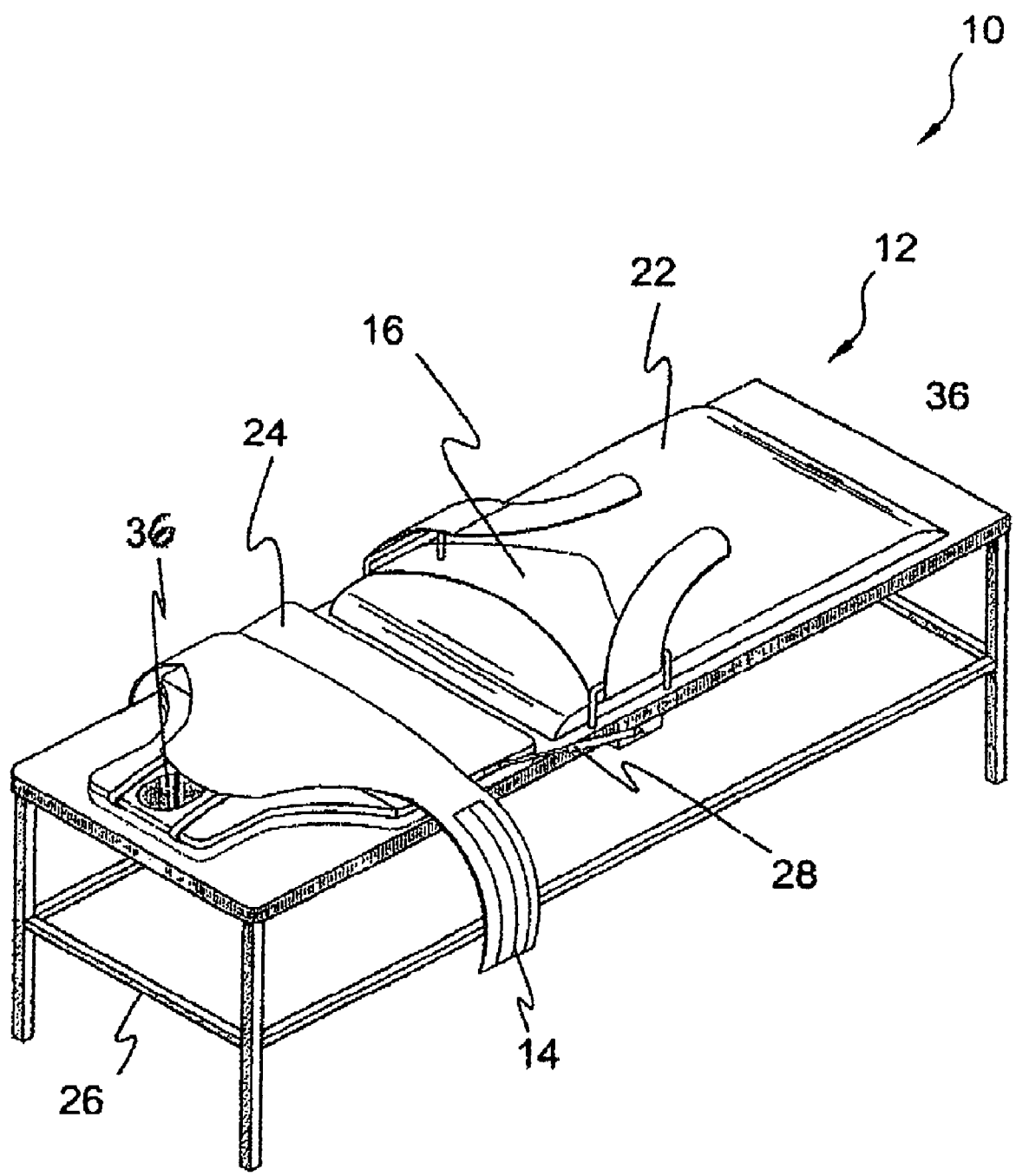
Figure 3:
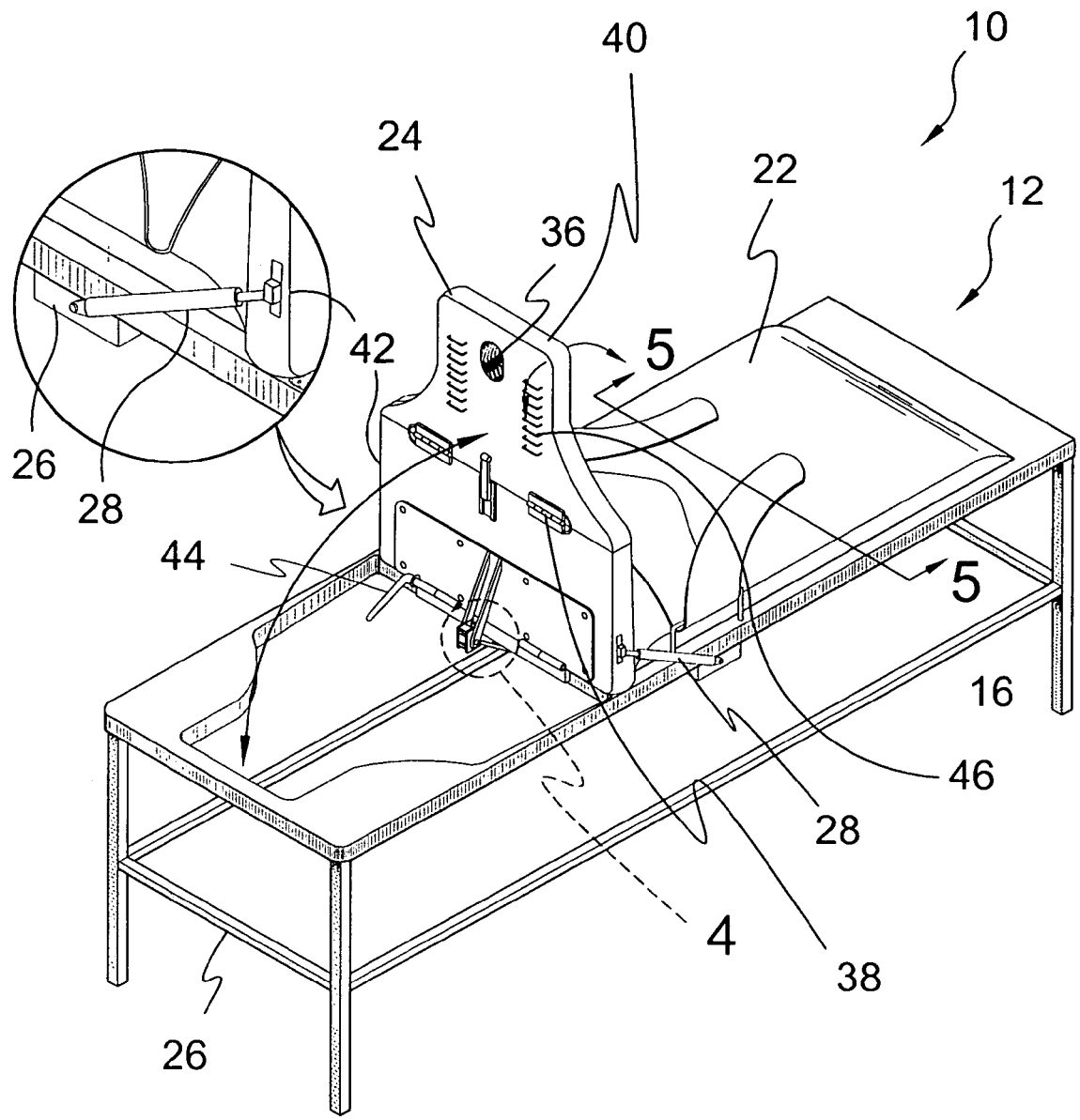
Figure 4:
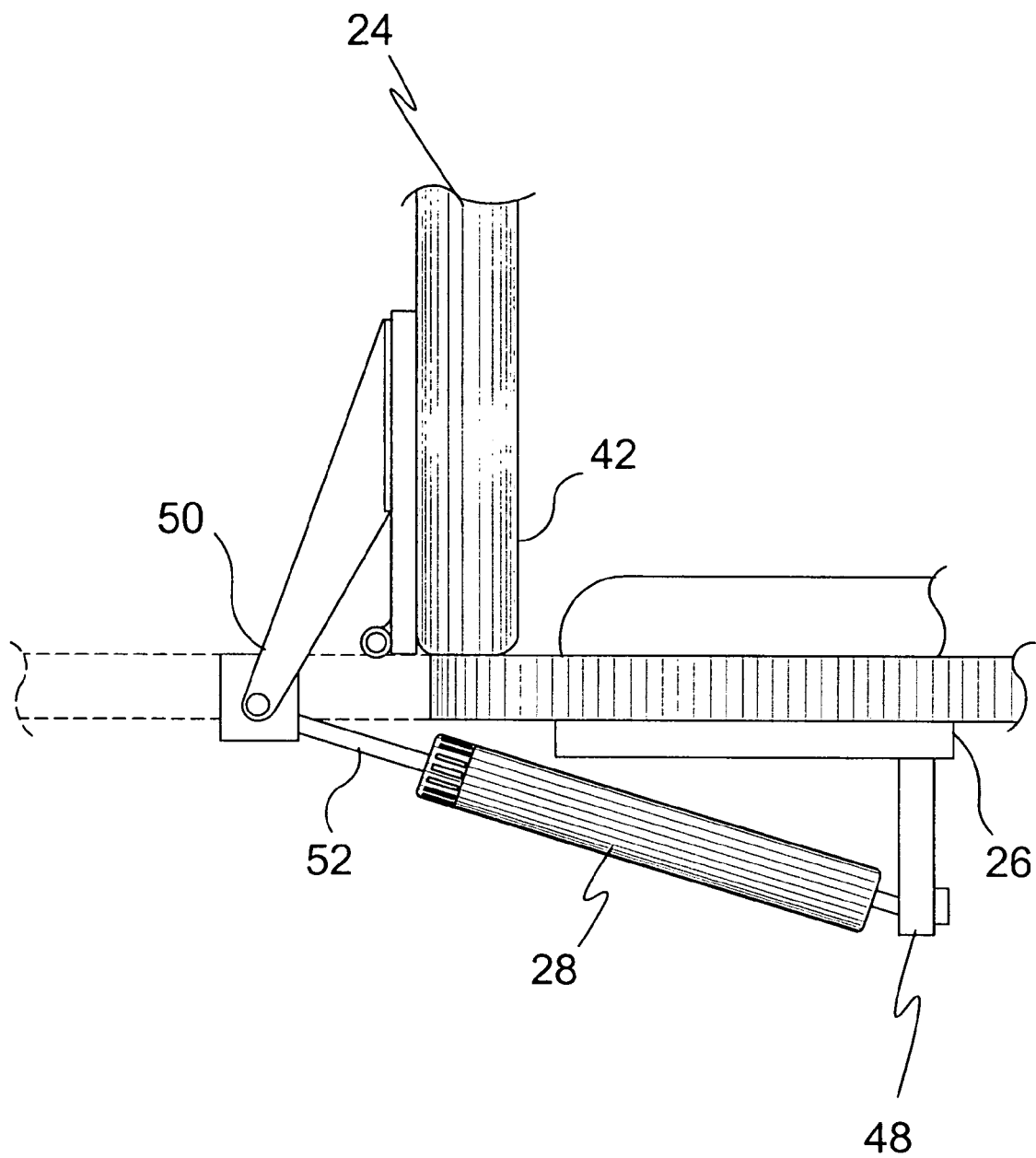
Figure 5:
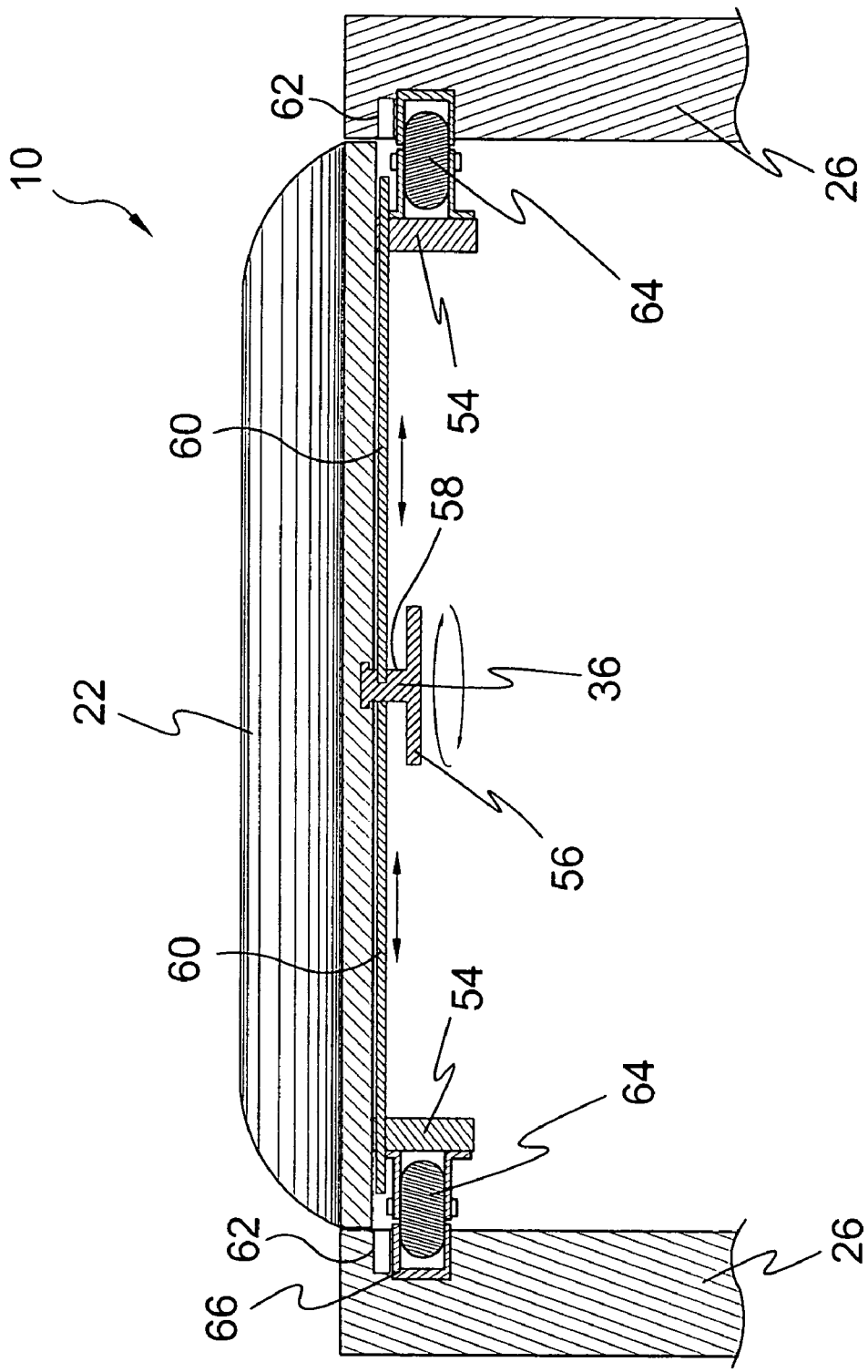
Figure 6:
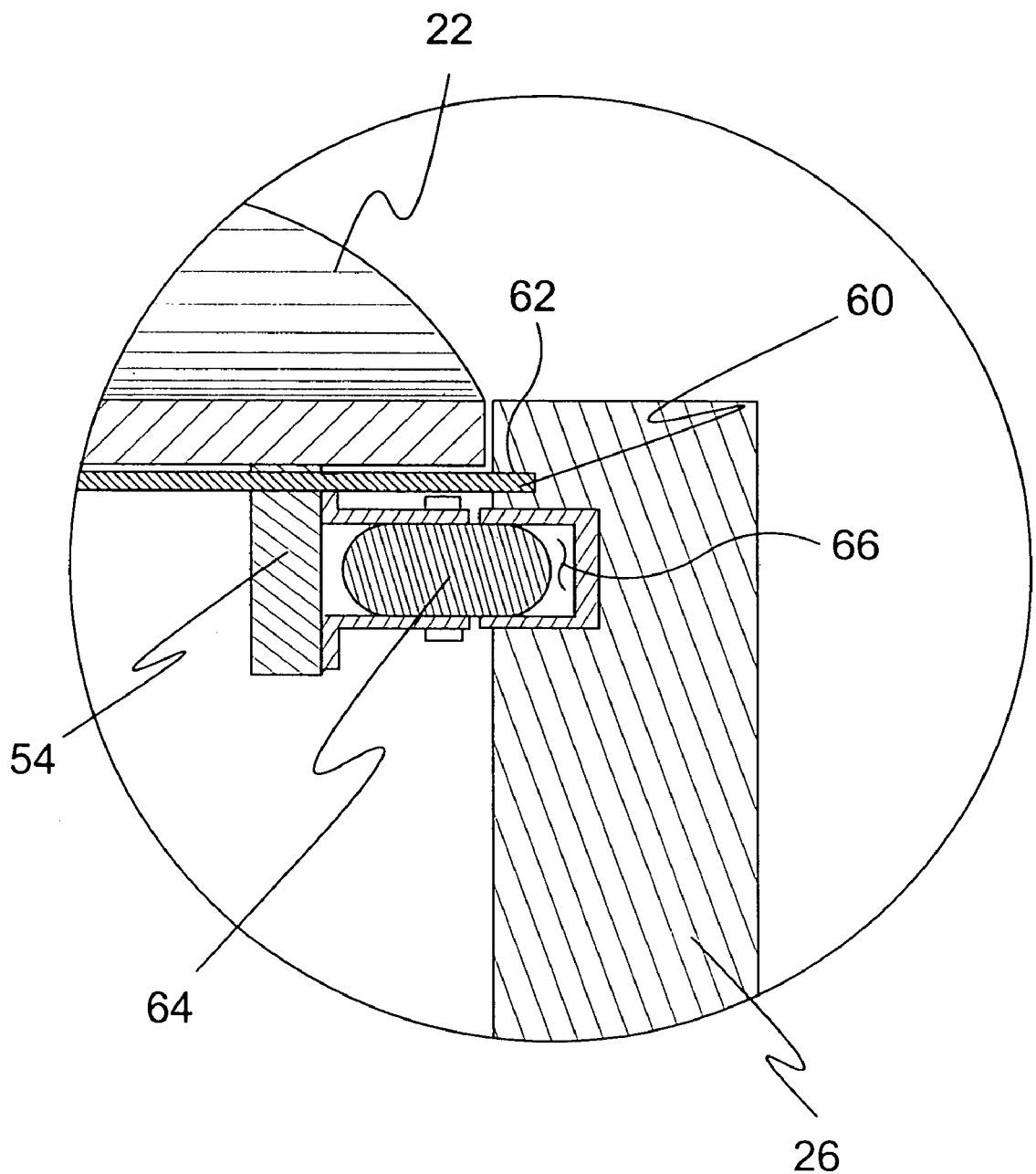
Figure 7:
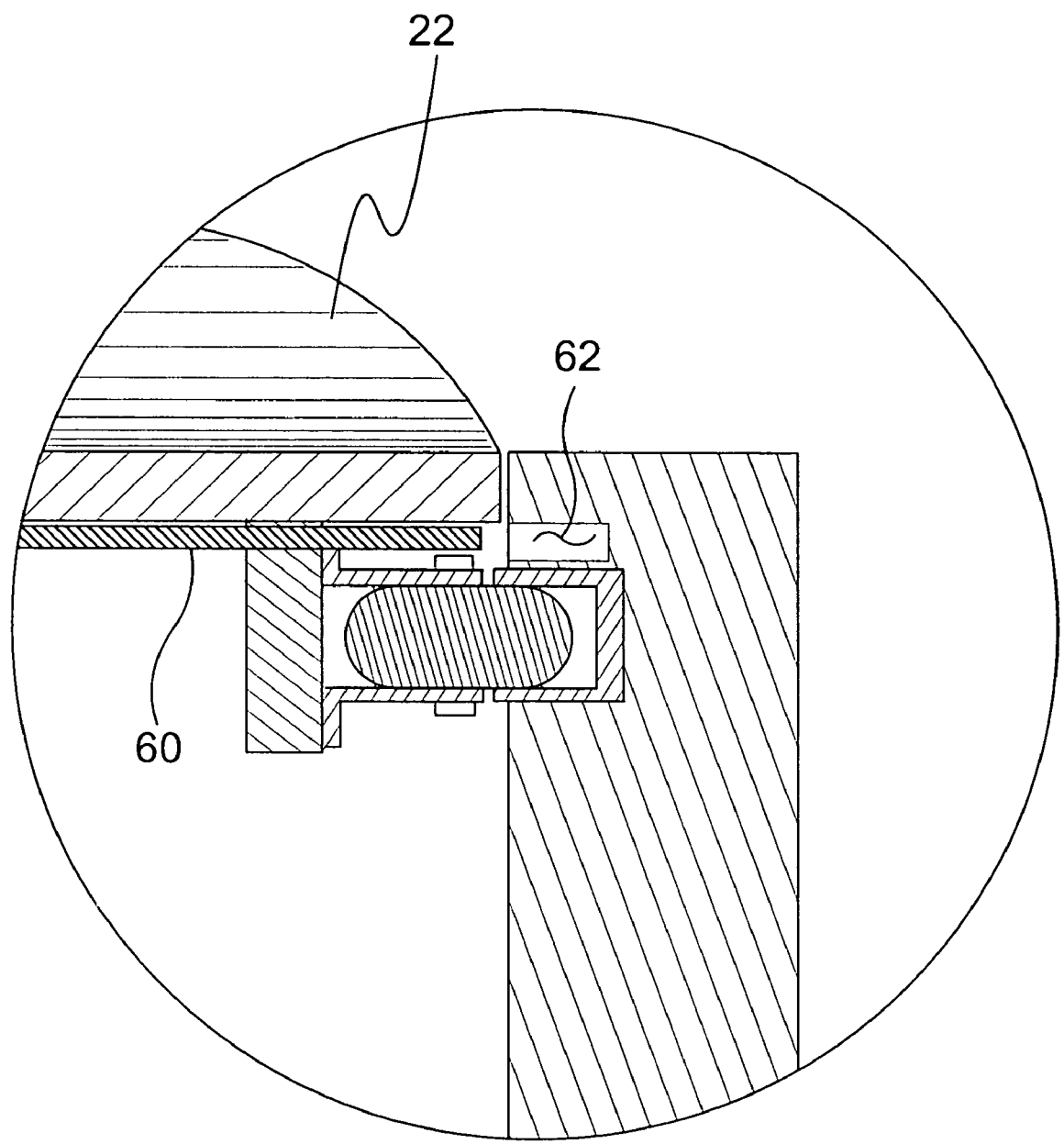
Figure 8:
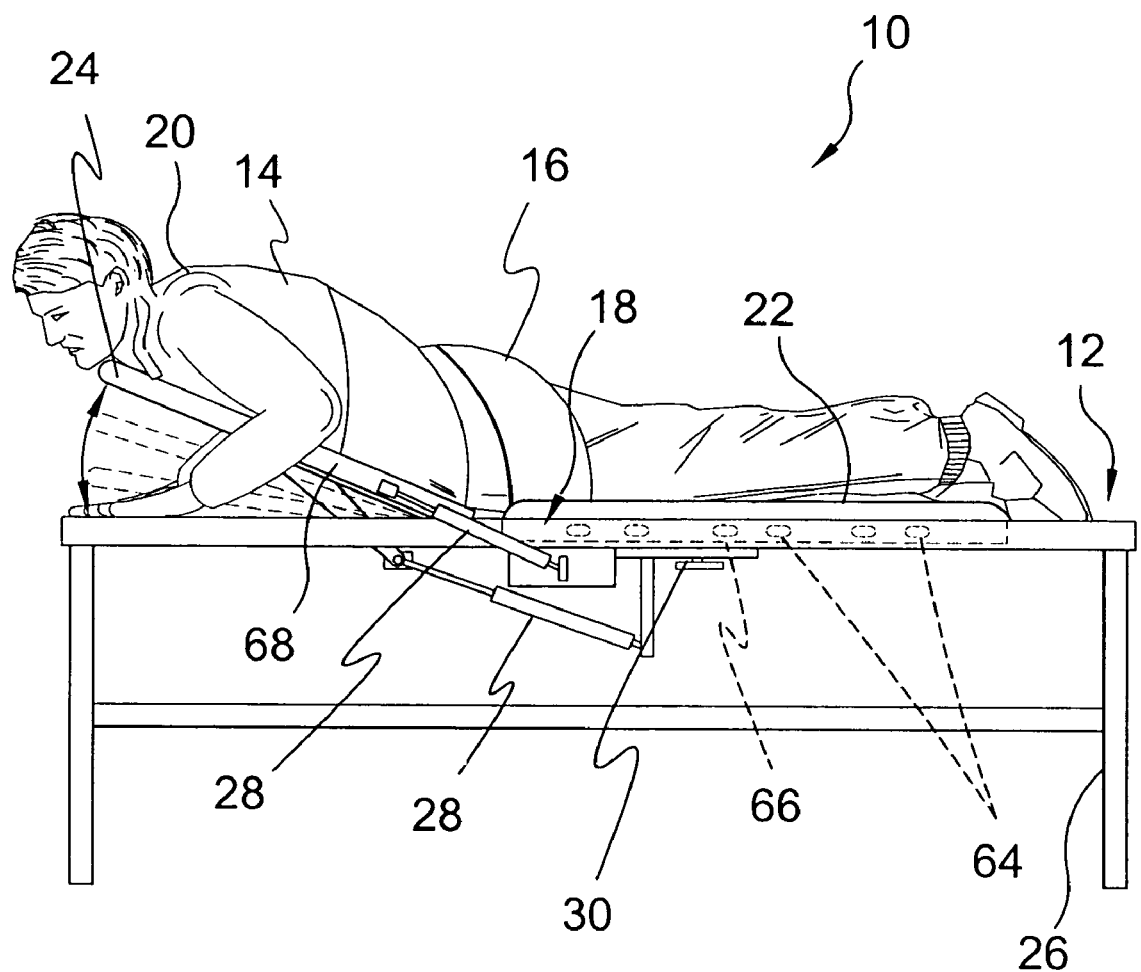
Figure 9:
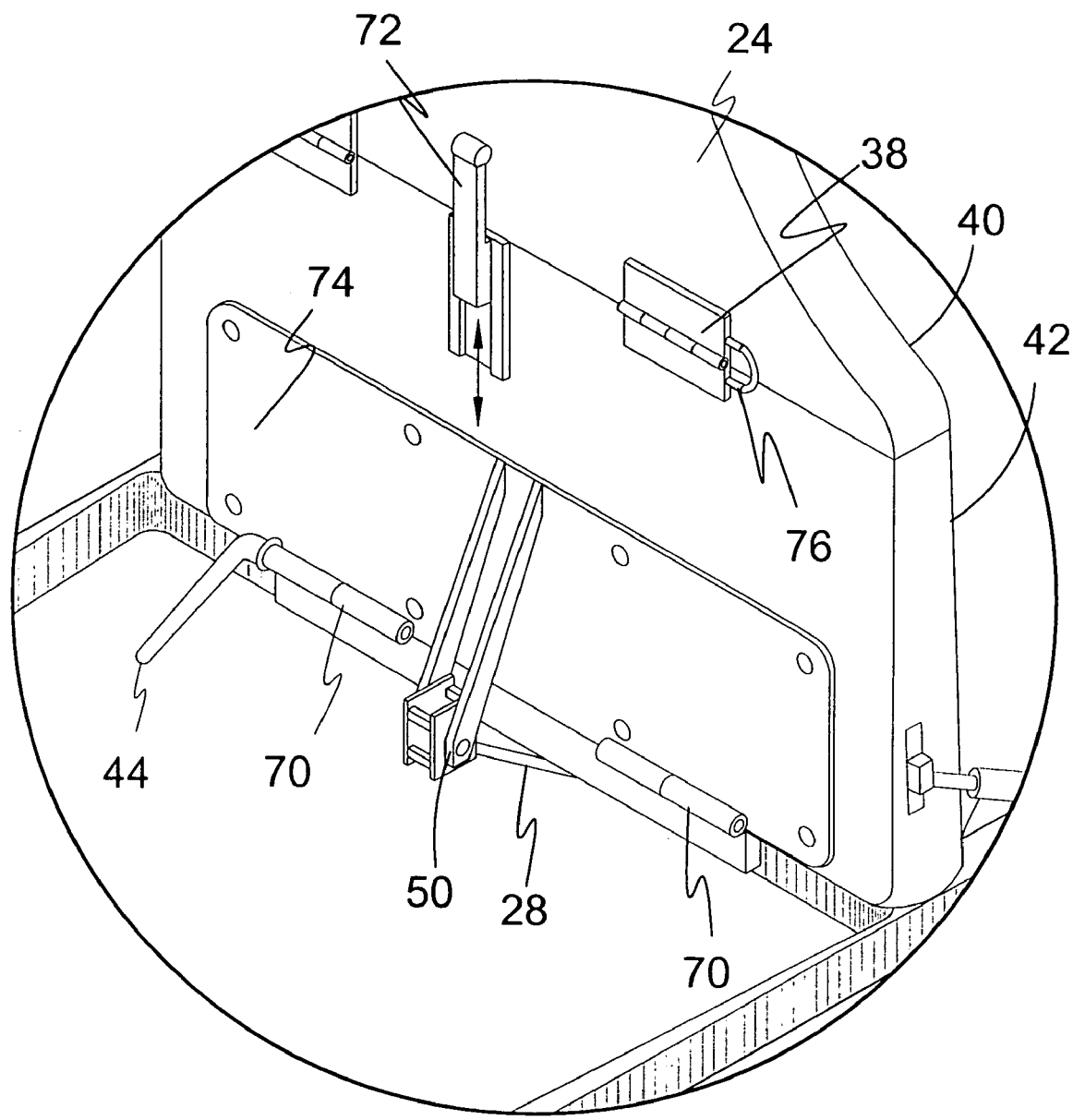
Figure 10:
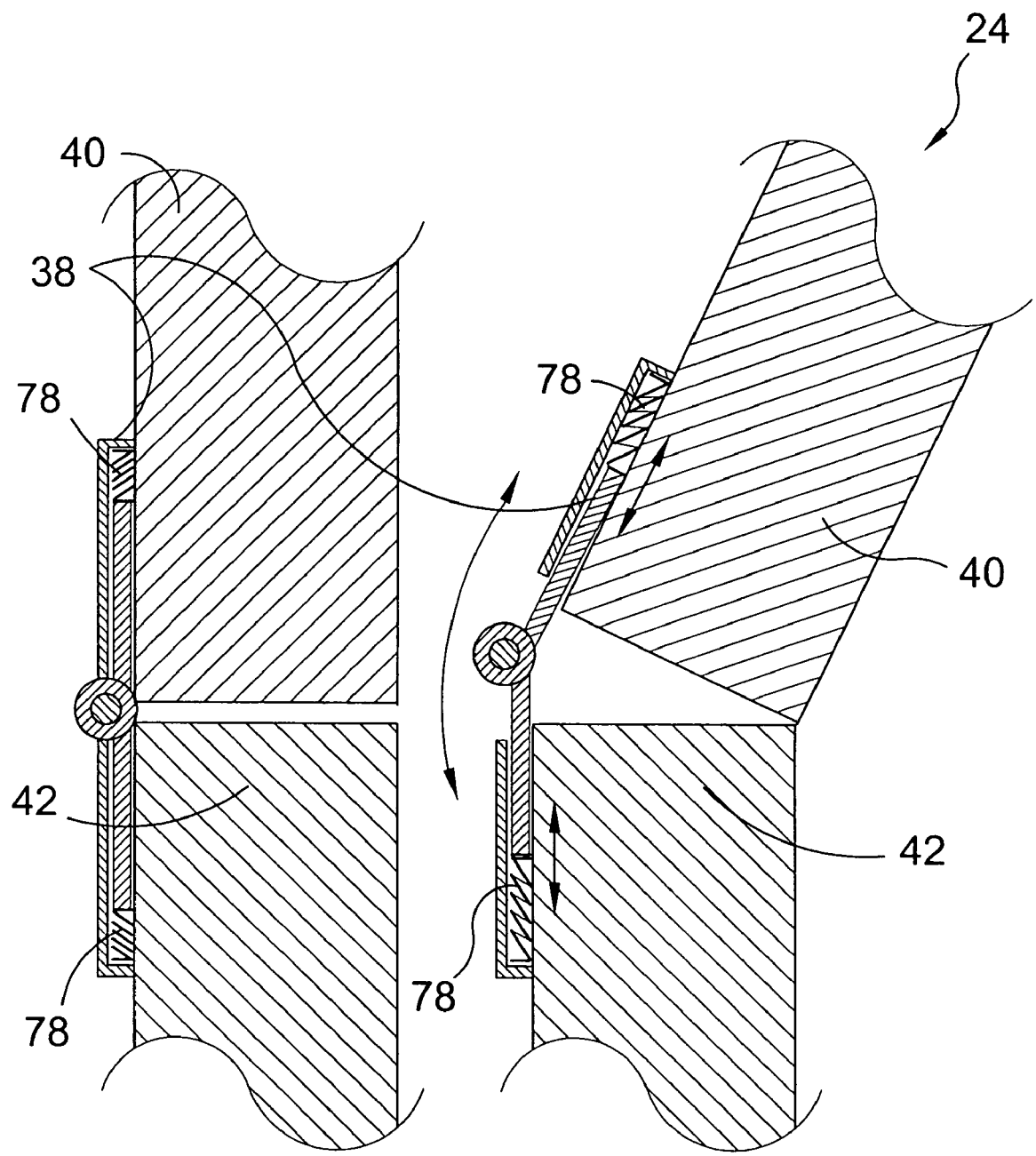
Figure 11:
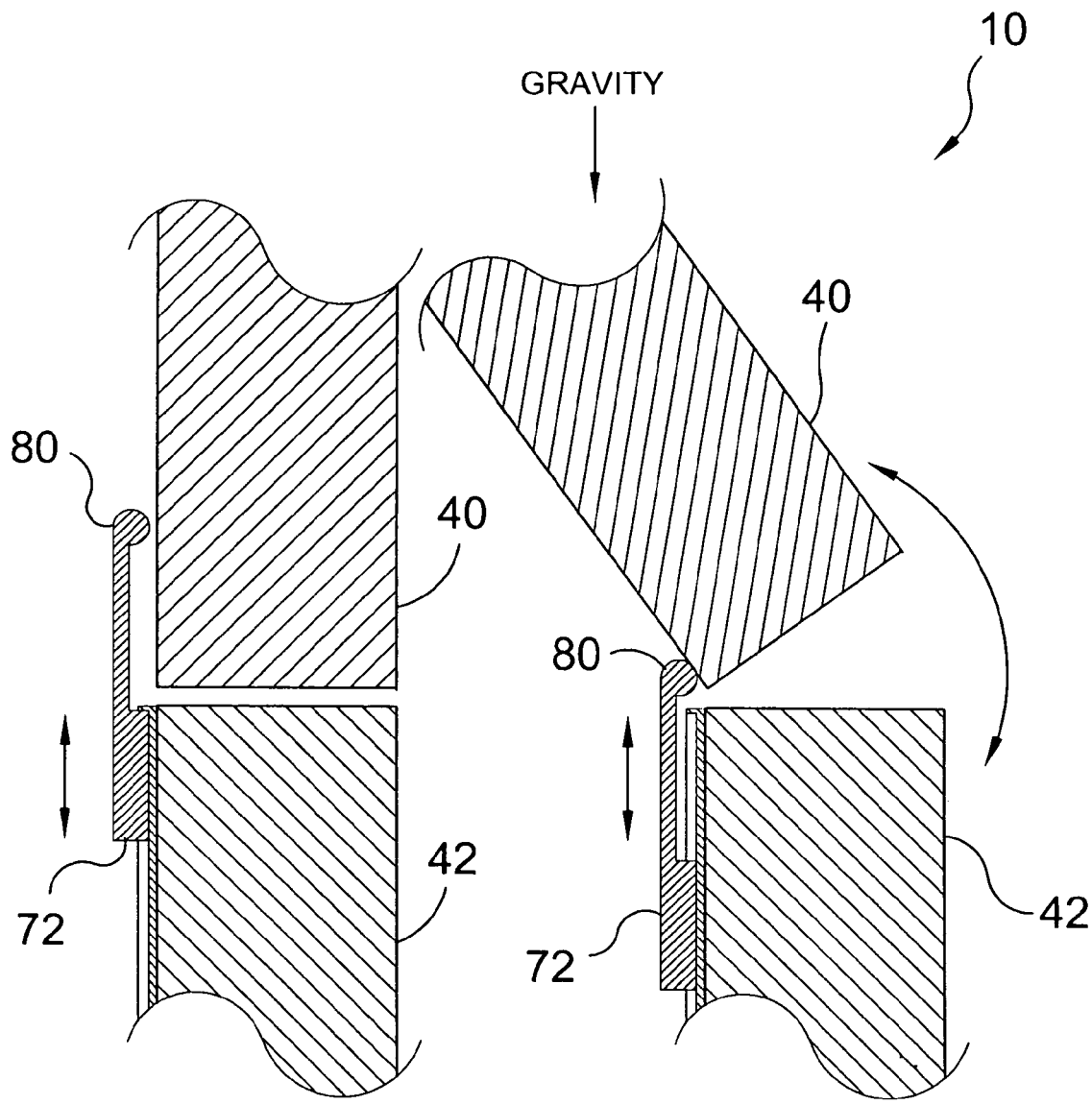

In order that the invention may be more fully understood, it will now be described, by way of example, with reference to the accompanying drawing in which:

FIG. 1 is an illustrative view of the present invention in use;
FIG. 2 is a perspective view of the present invention;
FIG. 3 is a perspective view of the present invention;
FIG. 4 is a detailed view of the present invention;
FIG. 5 is a perspective view of the present invention;
FIG. 6 is a detailed view of the lower cushion sliding mechanism of the present invention;
FIG. 7 is a detailed view of the lower cushion sliding mechanism of the present invention;
FIG. 8 is an illustrative view of the present invention in use;
FIG. 9 is a detailed view of the under side of the upper body cushion of the present invention;
FIG. 10 is a detailed sectional view of the spring loaded lockable hinge of the present invention; and
FIG. 11 is a detailed sectional view of the downward angle adjustment of the present invention.

DESCRIPTION OF THE REFERENCED NUMERALS

Turning now descriptively to the drawings, in which similar reference characters denote similar elements throughout the several views, the figures illustrate the Traction Extension Table of the present invention. With regard to the reference numerals used, the following numbering is used throughout the various drawing figures.

10 Traction Extension Table of the present invention
12 segmented table
14 chest harness
16 lumbar harness
18 tensioning assembly
20 patient
22 locking roller cushion
24 adjustable cushion
26 frame
28 variable resistance shock
30 locking mechanism
36 face recess
38 spring-loaded locking hinge
40 top section of 24
42 bottom section of
44 position lock
46 attachment hooks
48 shock bracket
50 pivoting shock arm
52 shaft of 28
54 roller assembly
56 handle of 30
58 shaft of 56
60 extension bar
62 locking aperture
64 roller
66 roller channel
68 arm cut-out
70 hinge
72 downward adjustment angle
74 cushion
76 lock release of 38
78 spring
80 bar of 72

DETAILED DESCRIPTION OF THE PREFERRED EMBODIMENT

The following discussion describes in detail one embodiment of the invention. This discussion should not be construed, however, as limiting the invention to those particular embodiments, practitioners skilled in the art will recognize numerous other embodiments as well. For definition of the complete scope of the invention, the reader is directed to appended claims.

FIG. 1 is an illustrative view of the present invention 10 in use. The present invention is a traction extension table 10 comprising a segmented table 12 a chest harness 14 and a lumbar harness 16 fastened thereto and a tensioning assembly extending therebetween to aid the patient 20 positioned on the table 12 to perform extension exercises. The table 12 is segmented into a locking roller cushion 22 and an adjustable cushion 24 mounted on a frame 26. The locking cushion 22 is pivotally connected to a central portion of the frame 26 adjacent to the locking cushion 22. Variable resistance shock absorbers 28 are secured to the frame 26 and the adjustable cushion 24 to control the rate of descent when in use. The chest harness 16 is attached via a spring to maintain the traction as the table comes up so there won't be any slack on the chest harness 16. The locking roller cushion 22 is slid into the desired position prior to usage and is secured in place by a locking mechanism 30.

FIG. 2 is a perspective view of the present invention 10. The present invention 10 is a segmented table 12 for patients to lie on that will maintain traction for lumbar discs and provides an easy way to perform extension exercises. The present invention is a traction extension table 10 comprising a segmented table 12 a chest harness 14 and a lumbar harness 16 fastened thereto and a tensioning assembly extending therebetween to aid the patient positioned on the table 12 to perform extension exercises. The table 12 is segmented into a locking roller cushion 22 and an adjustable cushion 24 mounted on top 34 portion of a frame 26. The locking cushion 22 is pivotally connected to a central portion of the frame 26 adjacent to the locking cushion 22. Variable resistance shock absorbers 28 are secured to the frame 26 and the adjustable cushion 24 to control the rate of descent when in use. The adjustable cushion 24 has a recess 36 into which the patients face is placed during therapy rather than having to turn the head. The chest harness 16 is attached via a spring to maintain the traction as the table comes up so there won't be any slack on the chest harness 16.

FIG. 3 is a perspective view of the present invention 10. The chest harness is secured to the adjustable cushion 24 and the lumbar harness 16 is attached to the locking roller cushion 22 for securing the patient to the segmented table 12. Traction for the lower portion of the body is achieved by sliding the locking roller cushion 22 into place and locking it in place. Traction on the upper portion of the body is maintained by chest harness 14 straps attached to springs on the back of the adjustable cushion 24. The adjustable cushion 24 is divided into a top portion 40 and a bottom portion 42 and includes a spring-loaded lockable hinge 38 that allows the user to determine and fix the angle of the top portion 40 relative to the bottom portion 42. A position lock 44 is disposed on the lower bottom portion 42 of the adjustable cushion 24 proximal the frame 26 and a plurality of attachment hooks 46 are disposed on the underside of the top portion 40 thereof for the attachment of springs thereto. The face recess 36 is included in the top portion 40 of the adjustable cushion 24. Also shown is the attachment means of the side shocks 28 with a connection to the frame 26 on one end and to the adjustable cushion 24 on the other.

FIG. 4 is a detailed view of the variable resistance, single dial shock 28 centrally disposed underneath the adjustable cushion 24. The shock 28 is secured to a shock bracket 48 integral with the frame 26 and the shaft is fastened to a pivoting shock arm 50 that is affixed on the other end to the bottom portion 42 of the adjustable cushion 24.

FIG. 5 is a sectional front view of the present invention 10 taken from FIG. 4 as indicated. Shown are the roller cushion locking mechanism 30 and the roller assembly 54 for the locking roller cushion 22. The locking mechanism 30 comprises a handle 56 with a shaft 58 rotatively connected to the underside of the roller cushion 22. A pair of offset extension bars 60 extend into locking apertures 62 disposed within the frame 26 when the handle 56 is turned in one direction, and retract therefrom when turned the other. A plurality of corresponding locking apertures 62 are disposed in spaced apart relation on their respective frame 26 members thereby permitting the user to position and secure the roller cushion 22 accordingly. The roller assembly 54 comprises a vertically oriented roller 64 associated with the bottom of the roller cushion 22 that travels within a channel 66 extending longitudinally within the frame 26.

FIG. 6 is a detailed view of the lower cushion sliding mechanism of the present invention. Shown is the extension bar 60 extended into the locking aperture 62 to lock the roller cushion 22 into position to give traction to the lower half of the body. The roller assembly 54 comprises a vertically oriented roller 64 associated with the bottom of the roller cushion 22 that travels within a channel 66 extending longitudinally within the frame 26.

FIG. 7 is a detailed view of the lower cushion sliding mechanism of the present invention. Shown is the extension bar 60 retracted from the locking aperture 62 to release the roller cushion 22

FIG. 8 is an illustrative view of the present invention 10 in use. The present invention is a traction extension table 10 comprising a segmented table 12 a chest harness 14 and a lumbar harness 16 fastened thereto and a tensioning assembly 18 extending therebetween to aid the patient 20 positioned on the table 12 to perform extension exercises. The table 12 is segmented into a locking roller cushion 22 and an adjustable cushion 24 mounted on a frame 26. The locking cushion 22 is pivotally connected to a central portion of the frame 26 adjacent to the locking cushion 22. Variable resistance shock absorbers 28 are secured to the frame 26 and the adjustable cushion 24 to control the rate of descent when in use. The chest harness 16 is attached via a spring to maintain the traction as the table comes up so there won't be any slack on the chest harness 16. The locking roller cushion 22 is slid into the desired position prior to usage due to integral rollers 64 that travel within roller channels 66 disposed in the frame 26 and is secured in place by a locking mechanism 30. The arms of the patient 20 extend through inside cut-outs 68 while performing the exercise.

FIG. 9 is a detailed view of the under side of the adjustable cushion 24. Shown is the underside of the hinged 70 adjustable cushion 24 having a single shock 28 to aid an individual positioned on said table to perform extension exercises. The adjustable cushion 24 is divided into a top section 40 and a bottom section 42 that are attached by spring-loaded lockable hinges 38 with lock releases 76. A downward angle adjustment 72 is situated therebetween specially suited to customize its angular displacement for proper support of the user's neck. A dial resistance shock 28 is secured to a pivoting shock arm 50 fastened to a base plate 74 disposed on the underside of the bottom portion 42 of the adjustable cushion 24 to incorporate means for varying the pressure of the tensioning member upon the pivotal table section.

FIG. 10 is a detailed sectional view of the spring 78 loaded lockable hinge 38. Depicted is the spring load hinge 38 in a retracted and extended position whereby the user may swing the hinged top section 40 of the adjustable cushion 24 upwardly or downwardly relative to the bottom section 42 wherethen the hinge 38 may be locked supporting the desired angled table section in a fixed position.

FIG. 11 is a detailed view of the downward angle adjustment 72. Shown is the downward angle adjustment 72 comprising a bar 80 bound to a track that may be slid up or down so as to cause the downwardly pivoting top section 40 of the adjustable cushion 24 to come to rest on the end of the bar 80 at a desired downward angle relative to the bottom section 42 and held to that locus by gravitational forces.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention

What is claimed is:

1. A traction extension table used to aid a patient in performing assisted lower back and abdominal extensions for the rehabilitation of bulging/herniated lumbar discs comprising:
    a) a frame having legs and a substantially flat top surface;
    b) a segmented table top disposed on top of said frame comprising:
        i) a horizontal locking roller cushion that slides longitudinally along said frame adapted to support a lower portion of a patient's body;
        ii) a pivotally adjustable cushion adjacent to said roller cushion capable of pivoting from a horizontal position to a substantially vertical position adapted to raise an upper portion of said patient's body using arms of a patient to push said pivotally adjustable cushion upwardly;
        iii) a tensioning assembly to regulate the rate of descent of said adjustable cushion while bearing weight during usage;
    c) a lumbar harness for securing the lower body portion to said roller cushion;
    d) a chest harness for securing the upper body portion to said pivotally adjustable cushion; and
    e) said pivotally adjustable cushion being divided into a top section and a lower section hingedly attached to each other, allowing said top section to pivot either upwardly or downwardly with respect to said bottom section for proper support of a patient's neck.

2. The action extension table recited in claim 1, wherein said tensioning assembly includes at least one variable resistance shock absorber being positioned for regulating the rate of descent of the pivotally adjustable cushion supporting the upper portion of the patient's body.

3. The traction extension table recited in claim 2, wherein said tensioning assembly includes three shock absorbers.

4. The traction extension table recited in claim 3, wherein two shock absorbers are disposed on opposing sides of said adjustable cushion with the shock absorbers secured to said frame and their respective shafts attached to said adjustable cushion.

5. The traction extension table recited in claim 4, wherein one shock absorber is disposed in a central location beneath said adjustable cushion with the shock absorber secured to a shock bracket emanating from said frame and the distal end of its respective shaft secured to a pivoting shock arm fastened to a hinged back plate on the underside of the bottom section of said adjustable cushion.

6. The traction extension table recited in claim 5, wherein said roller cushion further includes a plurality of rollers disposed on opposing sides thereof to enable the user to position it along the longitudinal plane of said frame as needed depending on the size of the patient.

7. The traction extension table recited in claim 6, wherein said rollers are horizontally disposed to ride along a roller channel incorporated within said frame.

8. The traction extension table recited in claim 7, wherein said roller cushion further includes a locking mechanism to secure it once placed in the desired position to provide traction for the lower half of said patient's body.

9. The traction extension table recited in claim 8, wherein said locking mechanism comprises:
    a) a handle;
    b) a shaft extending from said handle and rotatably secured to the underside of said roller cushion;
    c) a pair of offset extension bars pivotally connected to said shaft and extending in opposing direction towards the sides of said frame; and
    d) a plurality of spaced apart locking apertures disposed on the interior of each side of said frame corresponding in size and shape to accept said extension bars therein.

10. The traction extension table recited in claim 9, wherein said top section of said pivotally adjustable cushion has a pair of cut-out sections to allow said patient to extend arms straight down, and a recess between said cut-out sections to receive a face of said patient rather than requiring the patient to turn his head, thereby allowing the arms to be extended to lift the upper body portion while the lower portion is restrained thereby effectively compressing the lower spine.

11. The traction extension table recited in claim 10, wherein hinges connecting the top and bottom sections of said pivotally adjustable cushion are spring loaded resisting upward movement of said top section.

12. The traction extension table recited in claim 11, having a downward angle adjustment comprising a sliding bar mounted on said bottom section of said pivotally adjustable cushion that determines the angular downward displacement of said first section with respect to said second section for proper support of a patient's neck.

13. The traction extension table recited in claim 12, wherein said hinges connecting said top section and said bottom section of said pivotally adjustable cushion are lockable.

14. A method of aiding a patient obtaining traction in performing assisted lower back and abdominal extensions for the rehabilitation of bulging/herniated lumbar discs comprising the steps of:
    a) lying said patient face down on a table top of a frame having legs, said table top having into a horizontal locking roller cushion that slides longitudinally along said frame adapted to support a lower portion of a patient's body, a pivotally adjustable cushion adjacent to said roller cushion capable of pivoting front a horizontal position to a substantially vertical position supporting an upper portion of said patient's body, said pivotally adjustable cushion being divided into a top section and a lower section hingedly attached to each other, allowing said top section to pivot either upwardly or downwardly with respect to said bottom section for proper support of the patient's neck;

b) using a lumbar harness for securing the lower body portion to said roller cushion;
c) using a chest harness for securing the upper body portion to said pivotally adjustable cushion;
d) said patient using arms to push down on said frame to raise said pivotally adjustable cushion; and
e) said patient releasing arms allowing said pivotally adjustable cushion to descend, said frame having a tensioning assembly to regulate the rate of descent of said adjustable cushion while bearing weight during usage.

* * * * *